US00PP27392P2

(12) United States Plant Patent
Hanna et al.

(10) Patent No.: US PP27,392 P2
(45) Date of Patent: Nov. 15, 2016

(54) BERMUDAGRASS NAMED 'DT-1'

(50) Latin Name: *Cynodon transvaalensis×Cynodon dactylon*
Varietal Denomination: DT-1

(71) Applicants: Wayne W. Hanna, Chula, GA (US); Brian M. Schwartz, Tifton, GA (US)

(72) Inventors: Wayne W. Hanna, Chula, GA (US); Brian M. Schwartz, Tifton, GA (US)

(73) Assignees: University of Georgia Research Foundation, Inc., Athens, GA (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/545,732

(22) Filed: Jun. 10, 2015

(51) Int. Cl.
*A01H 5/12* (2006.01)

(52) U.S. Cl.
USPC ..... Plt./389

(58) Field of Classification Search
USPC ..... Plt./389
See application file for complete search history.

*Primary Examiner* — Annette Para
(74) *Attorney, Agent, or Firm* — Klarquist Sparkman, LLP

(57) ABSTRACT

Bermudagrass 'DT-1' is provided. The new and distinct upright variety has excellent drought tolerance, superior wear tolerance, small seed heads, and thrives in hot and humid conditions. The asexually reproduced triploid variety is reliably propagated vegetatively.

3 Drawing Sheets

ACKNOWLEDGMENT OF GOVERNMENT SUPPORT

This invention was made in part with U.S. Government support on behalf of U.S. Department of Agriculture, Hatch Act Grant No. 25-26-GF328-171. The U.S. Government has certain rights in this invention.

DESCRIPTION

Latin name: Bermudagrass 'DT-1' is an inter-specific hybrid of the genus and species *Cynodon transvaalensis*× *Cynodon dactylon.*

Variety denomination: The new bermudagrass is denominated 'DT-1'.

BACKGROUND

The present invention relates to a new and distinct cultivar of bermudagrass botanically known as *Cynodon transvaalensis*×*Cynodon dactylon*, and has been given the varietal name 'DT-1'. The new bermudagrass 'DT-1' is a product of a planned breeding program conducted by the Inventors in Tifton, Ga. The objective of the bermudagrass breeding program is to create new plant cultivars with improved commercial qualities. This cultivar is commercially important for its superior drought tolerance and other qualities, which are enumerated herein.

Pedigree and history: Several *C. transvaalensis parents* (unpatented) were crossed with several *C. dactylon* parents (unpatented) in Tifton, Ga. Crosses were made in the field by surrounding each *C. transvaalensis* parent with a *C. dactylon* parent in 6-square plots. All crosses were in close proximity, and resulted in somewhat random parentage of all resulting progeny. Progenies were planted from the cross combinations. Once established, the plots were mowed three times per week at a one-fourth inch height setting on the mower. Plants that maintained density, color, and drought tolerance were selected in the fall of the second year after planting. One of these selections, 'DT-1' (DT for drought tolerant), was identified and has been systematically tested since 2002 in three drought trials and two normal input trials in Tifton, Ga. Bermudagrass 'DT-1' has also been tested in a number of drought-stress trials, two traffic-stress trials, and irrigated, non-stress trials. Testing of the new variety has been performed in Georgia, Florida, North Carolina, Oklahoma, and Texas.

Asexual reproduction of the new bermudagrass 'DT-1' by vegetative terminal cuttings in a controlled environment in Tifton, Ga., since 1993, has shown that the unique features of this new bermudagrass are stable and reproduce true to type in successive generations.

SUMMARY

The cultivar 'DT-1' has not been observed under all possible environmental conditions. The phenotype may vary somewhat with variations in environment and cultural practices such as temperature and light intensity without, however, any variance in genotype. The following traits have been repeatedly observed and have been determined to be the unique combination of characteristics of 'DT-1':

1. Excellent drought tolerance;
2. Superior wear and traffic tolerance;
3. Fast growth rate;
4. Prolonged color retention;
5. Small seed head; and
6. Thrives in hot and humid conditions.

'DT-1' has been compared to a number of grasses as discussed and set forth in Tables below.

Some data are by means of multi-ratings. In Tifton, Ga. ratings were taken monthly from April to October. No insecticides, fungicides or herbicides, except for one pound per acre of atrazine in March, were used on the grasses to which the comparisons were made and comparative data generated. The "turf quality" rating is a general rating wherein density, color, texture, pest resistance are considered for evaluating the desirability of the turf.

Comparison to 'Tift 419' (unpatented): 'DT-1' most closely resembles 'Tift 419'. 'DT-1' has significantly more drought tolerance than 'Tift419', especially during the first year of establishment. 'DT-1' has significantly better initial wear and traffic tolerance, and potential to recover more quickly from wear and traffic than 'Tift 419'. Turf quality of 'DT-1' is as good, or better than for 'Tift 419', particularly during drought stress. Plant color of 'DT-1' is similar or lighter than for 'Tift 419', depending on soil fertility levels. In most years, 'DT-1' tends to produce significantly more seed heads than 'Tift 419'.

Comparison to 'Tift 94'(U.S. Plant Pat. No. 10,079): 'DT-1' has significantly more drought tolerance than 'Tift 94'. 'DT-1' has significantly better initial wear and traffic tolerance, and potential to recover more quickly from wear and traffic than 'Tift 94'. Turf quality of 'DT-1' is as good, or better than for 'Tift 94', particularly during drought stress. Plant color of 'DT-1' is similar or lighter than for 'Tift 94', depending on soil fertility levels. In most years, 'DT-1' tends to produce significantly more seed heads than 'Tift 94'.

Comparison to 'ST-5' (U.S. Plant Pat. No. 21,017): 'DT-1' has significantly better wear and traffic tolerance than 'ST-5'. 'DT-1' does not have a dwarf-type plant stature like 'ST-5', and has a significantly faster growth rate than 'ST-5', which results in taller unmowed canopy heights during the growing season. Plant color of 'DT-1' is lighter than for 'ST-5'. In most years, 'DT-1' tends to produce significantly less seed heads than 'ST-5'.

Comparison to 'Riley's Super Sport' (U.S. Plant Pat. No. 11,181): 'DT-1' has significantly better wear and traffic tolerance than 'Riley's Super Sport'. 'DT-1' has a taller unmowed canopy height than 'Riley's Super Sport' during the growing season. Plant color of 'DT-1' is lighter than for 'Riley's Super Sport'. In most years, 'DT-1' and 'Riley's Super Sport' tend to produce similar number of seed heads, although the seed heads of 'DT-1' are generally more diminutive than observed for 'Riley's Super Sport'.

Comparison to other cultivars: 'DT-1' has superior turfgrass performance than 'Tifton 10' (unpatented), 'Princess-77' (unpatented, Plant Variety Protection Act Certificate 9500227), common bermudagrass (unpatented) and 'Latitude 36' (U.S. Plant Pat. No. 24,271), in short and long term drought environments (Table 3 and 4), and has equal turfgrass performance to 'Riley's Super Sport' and 'Latitude 36' when well-maintained through irrigation, fertilization and mowing (Table 3, Table 4 and FIG. 1). 'DT-1' has better traffic tolerance than 'Patriot' (U.S. Plant Pat. No. 16,801) and 'Discovery' (patent believed to be pending).

Comparison to Parents: 'DT-1' is, for the most part, intermediate in characteristics to its parents. 'DT-1' has the upright growth habit of the female parent, *C. transvaalensis*, and the rhizomes, persistence, and toughness of the male parent (*C. dactylon*). The inflorescence of 'DT-1' is a panicle. The anthers are spongy and non-dehiscent due to the sterility typical of triploids.

TABLE 1

Summary of inflorescence morphology of 'DT-1' bermudagrass compared to selected other bermudagrass genotypes measured during 2011 and 2012 in Tifton, GA.

| Genotype | Inflorescences per $m^2$ number | Inflorescence peduncle length mm | Racemes per inflorescence number | Raceme length mm | Florets per raceme number |
|---|---|---|---|---|---|
| '93-175' (unpatented) | 285 c[1] | 87 a | 4.4 a | 32 b | 25.0 b |
| 'Riley's Super Sport' | 3679 ab | 66 b | 3.6 b | 36 a | 38.3 a |
| 'DT-1' | 2940 b | 67 b | 2.9 c | 22 d | 13.2 d |
| 'ST-5' | 4232 a | 62 b | 2.3 d | 22 d | 15.6 cd |
| 'Tift 94' | 535 c | 53 c | 2.8 c | 25 c | 16.3 c |
| 'Tift 419' | 407 c | 48 c | 2.8 c | 25 c | 16.8 c |

[1]Means followed by the same letter are not significantly different according to Fisher's LSD (P = 0.05).

TABLE 2

Summary of vegetative plant morphology of 'DT-1' bermudagrass compared to selected other bermudagrass genotypes measured during 2011 in Tifton, GA.

| Genotype | Turf canopy height[1] cm | Leaf width[2] mm | Stolon internode length[3] mm |
|---|---|---|---|
| '93-175' | 12 b[4] | 1.8 b | 28 a |
| 'Riley's Super Sport' | 9 b | 2.2 a | 25 ab |
| 'DT-1' | 17 a | 1.8 b | 17 c |
| 'ST-5' | 9 b | 2.0 ab | 18 c |
| 'Tift 94' | 10 b | 1.8 b | 25 ab |
| 'Tift 419' | 9 b | 1.9 b | 21 be |

[1]Turf canopy heights were measured from the ground to the top of the leaves.
[2]Leaf widths were measured on the first fully expanded leaf of a mature phytomer in the turf canopy.
[3]Stolon internode lengths were measured between the $3^{rd}$ and $4^{th}$ node of the apical meristem.
[4]Means followed by the same letter are not significantly different according to Fisher's LSD (P = 0.05).

TABLE 3

Mean establishment, non-stressed and stress turfgrass quality of three bermudagrasses mowed at 5.1 cm (2.0 in) in field trials[1] at 7 locations across the U.S. during 2011, 2012, and 2013.

| Genotype | Establishment[2] South[5] | Establishment[2] North[6] | Establishment[2] All | Turf quality[3] South | Turf quality[3] North | Turf quality[3] All |
|---|---|---|---|---|---|---|
| | % green cover | | | Visual rating | | |
| 'Riley's Super Sport' | 55 a[7] | 66 ab | 62 a | 5.8 bc | 6.1 b | 5.9 c |
| 'DT-1' | 58 a | 75 a | 69 a | 7.3 a | 7.3 a | 7.3 a |
| 'Latitude 36' | 26 b | 59 bc | 46 b | 5.5 c | 7.0 a | 6.4 b |

| Genotype | Stress turf quality[4] South | Stress turf quality[4] North | Stress turf quality[4] All |
|---|---|---|---|
| | Visual rating | | |
| 'Riley's Super Sport' | 3.4 b | 4.2 b | 3.9 b |
| 'DT-1' | 5.9 a | 6.0 a | 5.9 a |
| 'Latitude 36' | 3.7 b | 3.8 b | 3.8 b |

[1]Field trials were planted in 2011. All trials were planted again in 2012 to repeat the experiments.
[2]Turfgrass establishment was visually rated on a 1-100% scale during year 1 of both trials.
[3]Turf quality was rated on a 1 to 9 scale with 1 = dead, 6 = acceptable, and 9 = excellent prior to the initiation of drought screening during year 2 in both trials.
[4]Stress turf quality cover was rated on a 1 to 9 scale with 1 = dead, 6 = acceptable, and 9 = excellent after varying days of drought stress, depending on location and soil type, during year 2 in both trials.

TABLE 3-continued

Mean establishment, non-stressed and stress turfgrass quality of three bermudagrasses mowed at 5.1 cm (2.0 in) in field trials[1] at 7 locations across the U.S. during 2011, 2012, and 2013.

[5]Testing locations were in College Station, TX, Gainesville, FL, and Tifton, GA.
[6]Testing locations were in Dallas, TX, Griffin, GA, Raleigh, NC, and Stillwater, OK.
[7]Means within columns followed by the same letter aren't significantly diff. acc. to Fisher's LSD (P ≤ 0.05).

TABLE 4

Mean turfgrass quality of 5 bermudagrass varieties mowed at 3.8 cm (1.5 in) averaged over 4 dates in 2010, 2011, and 2012 after sustained droughty conditions in the Linear Gradient Irrigation System (LGIS) evaluation at West Florida Research & Education Center (WFREC) in Jay, FL[1].

| | Irrigation level (% $ET_0$) | | | | |
|---|---|---|---|---|---|
| Genotype | 120 | 105 | 80 | 54 | 37 |
| | Visual rating[2] | | | | |
| 'Riley's Super Sport' | 4.7 b[3] | 4.5 bc | 4.3 b | 3.9 bc | 3.7 bc |
| common Bermuda-grass | 4.7 b | 4.1 bc | 4.1 b | 3.8 bc | 3.6 cd |
| 'DT-1' | 6.8 a | 6.6 a | 6.4 a | 6.3 a | 6.3 a |
| 'Princess- 77' | 4.7 b | 4.6 b | 4.3 b | 4.3 b | 4.1 b |
| 'Tifton 10' | 4.2 c | 4.0 c | 3.9 b | 3.6 c | 3.3 d |

| | Irrigation level (% $ET_0$) | | | |
|---|---|---|---|---|
| Genotype | 25 | 13 | 3 | Average |
| | Visual rating[2] | | | |
| 'Riley's Super Sport' | 2.8 c | 2.1 c | 2.2 c | 3.5 |
| common Bermuda-grass | 2.9 c | 2.4 c | 2.2 c | 3.5 |
| 'DT-1' | 5.8 a | 4.7 a | 4.6 a | 5.9 |
| 'Princess- 77' | 3.9 b | 3.1 b | 2.9 b | 4.0 |
| 'Tifton 10' | 2.7 c | 2.3 c | 2.2 c | 3.3 |

[1]Field trials were planted during 2010.
[2]Turf quality was rated on a 1 to 9 scale with 1 = dead, 5 = acceptable, and 9 = excellent.
[3]Means within columns followed by the same letter aren't significantly diff. acc. Fisher's LSD (P ≤ 0.05).

The foregoing and other objects, features, and advantages of the invention will become more apparent from the following detailed description, which proceeds with reference to the accompanying figures.

DETAILED DESCRIPTION

Botanical Description

Figure 1:
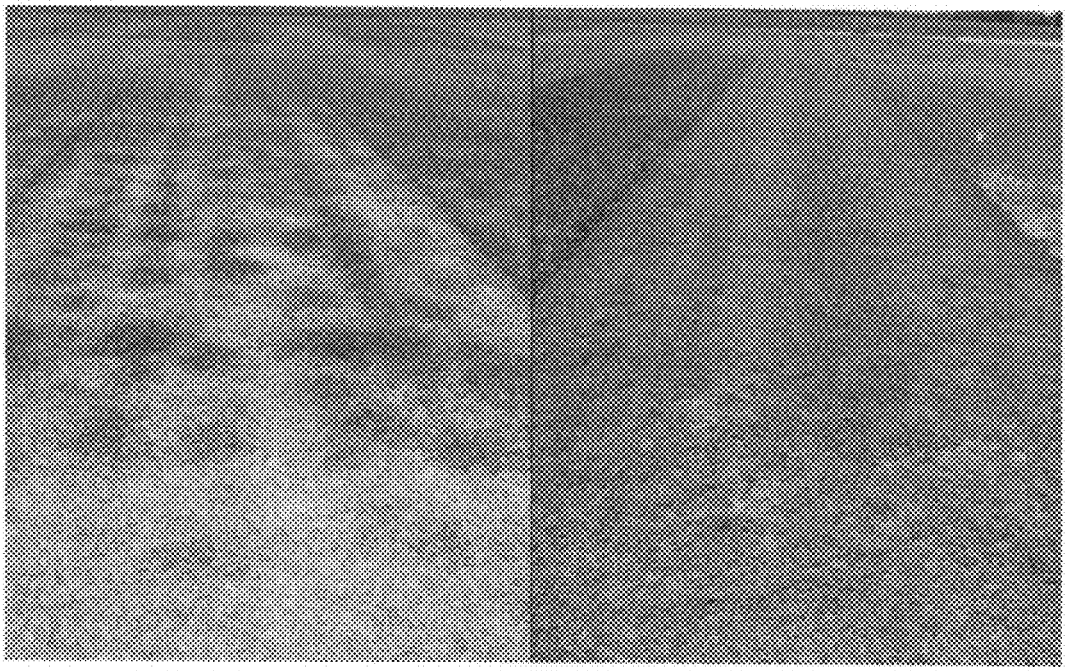
FIG. 1 is a photograph of 'Riley's Super Sport' (on the left) and 'DT-1' (on the right) bermudagrasses mowed at 3.8 cm (1.5 in) after sustained drought conditions in the Linear Gradient Irrigation System (LGIS) evaluation during 2011 at the West Florida Research and Education Center (WFREC) in Jay, Fla. Field trial planted from sod during 2010.
Figure 2:
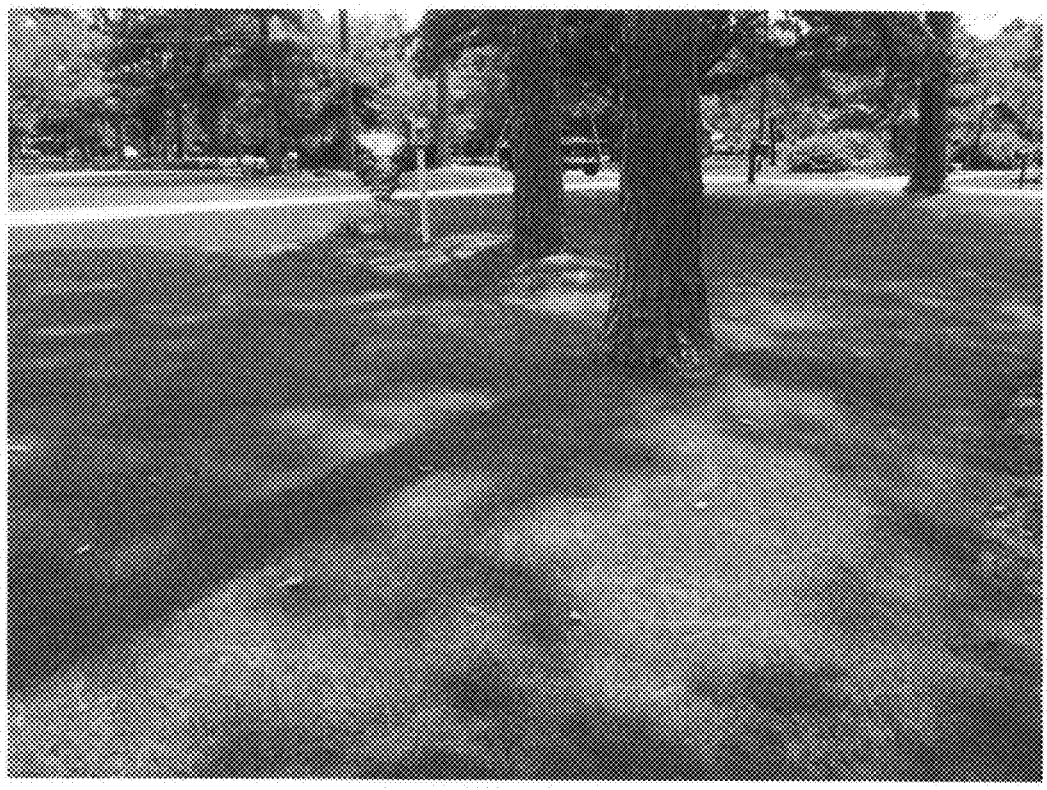
FIG. 2 is a photograph of 'DT-1' bermudagrass mowed at 5.1 cm (2.0 in) in an unirrigated lawn during 2013 in Tifton, Ga. Lawn planted from sprigs during 2012.
Figure 3:
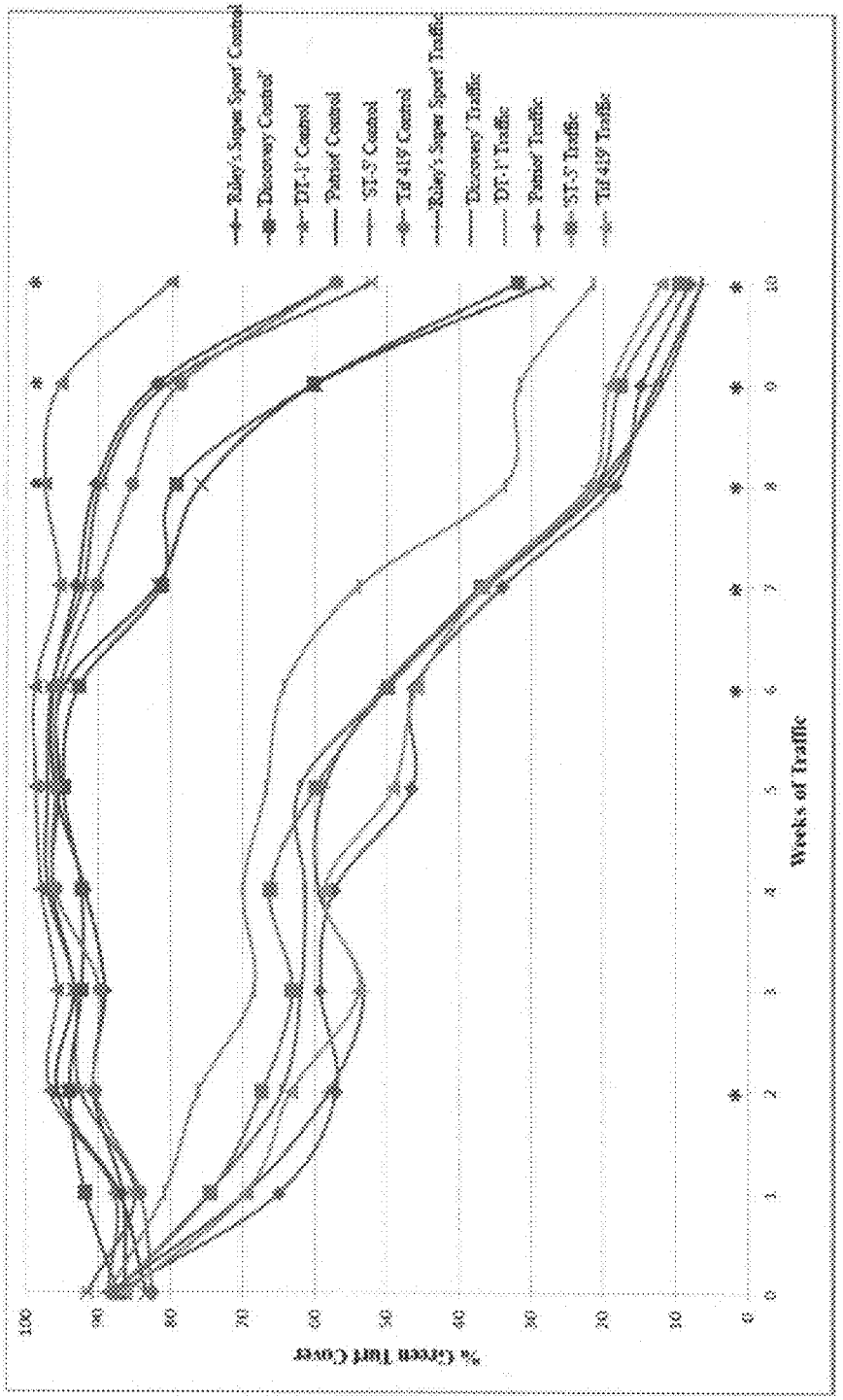
FIG. 3 is a graph showing mean turfgrass cover determined by digital image analysis (DIA) of 6 bermudagrasses mowed at 2.54 cm (1.0 in) over 10 weeks with and without traffic in an irrigated field trial during the fall of 2012 & 2013 in Tifton, Ga. Mean turfgrass cover of 'DT-1' is significantly greater than all other tested cultivars within respective wear treatments according to Fisher's LSD (P≤0.05) where * are present on the lower X-axis (wear treatment) and upper X-axis (control treatment). Field trials were planted during 2011.

The following observations, measurements, and values describe plants grown in Tifton, Ga. During the growing of the plants, typical day temperatures ranged from 69° F. to 99° F. and typical night temperatures ranged from 47° F. to 70° F. Plants were mowed at one half to one and a half inches in height, usually once or twice during the growing season. 'DT-1' was fertilized with about 1 pound of nitrogen per month.

'DT-1' has leaf color which most fits the Green Group 137B of The Royal Horticultural Society (R.H.S.) Colour Chart, 5$^{th}$ Edition. 'DT-1' is a triploid hybrid, which rarely produces seed or pollen, despite the fact that it produces more seed heads than some varieties. It is vegetatively propagated, ordinarily by sprigs or sod.

'DT-1' has greater inflorescence density than 'Tift 419' or 'Tift 94'. The inflorescence of 'DT-1' is taller than that of 'Tift 419' or 'Tift 94'. 'DT-1' has a similar number of racemes per flower as does 'Tift 419' and 'Tift 94'. 'DT-1' has a raceme length that is less than that of 'Tift 419' or 'Tift 94'.

In addition to the data provided in the Summary of the Invention, bermudagrass 'DT-1' produces a small seed head on a thin peduncle in late May and June, which is typical of bermudagrasses in general, but 'DT-1' produces slightly more seed heads than desired. Treatment with the plant growth regulator trinexapac-ethyl will cause a reduction in number of seed heads. Scalping of the turf canopy can also be a problem for bermudagrasses in general, but especially for 'DT-1' when adequate or excessive soil moisture and fertilizer are available to the plant. This can be addressed by proper management.

Additionally, 'DT-1' has been test grown in non-replicated drought situations. It has performed with acceptable turf quality where limited soil water and fertility have caused 'Riley's Super Sport', 'ST-5', 'Tift 94', and 'Tift 419' to have unacceptable turf quality or enter stress-induced dormancy. Persistence and growth through years with drought stress in several environments where soil erosion has been prevalent is also a desirable characteristic of 'DT-1' sod.

The un-replicated test plantings were: on sod farms in Poteet, Tex. since 2011, in Marshallville, Ga. since 2012, in Perry, Ga. since 2012, and in Lakeland, Ga. since 2013; in a residential lawn in Tifton, Ga. since 2012; on golf courses in Tifton, Ga. since 2012, in Richmond Hill, Ga. since 2012, in Atlanta, Ga. since 2012, in Valdosta, Ga. since 2013, and in Savannah, Ga. since 2013.

We claim:

1. A new and distinct variety of the bermudagrass named 'DT-1', substantially as illustrated and described herein.

* * * * *

'Riley's Super Sport' Bermudagrass

'DT-1' Bermudagrass